US011202664B2

(12) United States Patent
Finley

(10) Patent No.: US 11,202,664 B2
(45) Date of Patent: Dec. 21, 2021

(54) COMPRESSION FORCE MAGNIFIER

(71) Applicant: Nextremity Solutions, Inc., Warsaw, IN (US)

(72) Inventor: Adam Finley, Winona Lake, IN (US)

(73) Assignee: NEXTREMITY SOLUTIONS, INC., Warsaw, IN (US)

( * ) Notice: Subject to any disclaimer, the term of this patent is extended or adjusted under 35 U.S.C. 154(b) by 224 days.

(21) Appl. No.: 16/222,477

(22) Filed: Dec. 17, 2018

(65) Prior Publication Data

US 2020/0187997 A1    Jun. 18, 2020

(51) Int. Cl.
| | | |
|---|---|---|
| *A61B 17/80* | (2006.01) | |
| *A61B 17/88* | (2006.01) | |
| *A61B 17/68* | (2006.01) | |
| *A61B 17/56* | (2006.01) | |
| *A61B 17/86* | (2006.01) | |

(52) U.S. Cl.
CPC ...... *A61B 17/8019* (2013.01); *A61B 17/8872* (2013.01); *A61B 17/8014* (2013.01); *A61B 17/8033* (2013.01); *A61B 17/8061* (2013.01); *A61B 17/8665* (2013.01); *A61B 17/8695* (2013.01); *A61B 2017/564* (2013.01); *A61B 2017/681* (2013.01)

(58) Field of Classification Search
CPC ............ A61B 17/8004; A61B 17/8014; A61B 17/8061; A61B 17/8019; A61B 17/8695; A61B 17/8033; A61B 17/8047; A61B 17/8872; A61B 17/8665; A61B 2017/681
USPC ............ 606/70–71, 280, 282, 286, 288, 281
See application file for complete search history.

(56) References Cited

U.S. PATENT DOCUMENTS

| | | |
|---|---|---|
| 3,528,085 A | 9/1970 | Reynolds, Jr. |
| 3,866,607 A | 2/1975 | Forsythe et al. |
| 4,388,921 A | 6/1983 | Sutter et al. |
| 4,705,031 A | 11/1987 | Wolter |
| 4,957,496 A | 9/1990 | Schmidt |
| 5,486,176 A | 1/1996 | Hildebrand et al. |
| 6,533,786 B1 | 3/2003 | Needham et al. |
| 6,723,098 B1 | 4/2004 | Shah |
| 8,167,919 B2 | 5/2012 | Foley et al. |
| 8,257,403 B2 | 9/2012 | Den Hartog et al. |
| 8,257,406 B2 | 9/2012 | Kay et al. |
| 8,414,582 B2 | 4/2013 | Overes et al. |
| 8,747,443 B2 | 6/2014 | Aferzon |

(Continued)

FOREIGN PATENT DOCUMENTS

EP    0016338 A1    2/1980

OTHER PUBLICATIONS

UK Search Report dated Jun. 12, 2020 based on GB 1918520.6 (1 p.)

*Primary Examiner* — Marcela I. Shirsat
(74) *Attorney, Agent, or Firm* — Heslin Rothenberg Farley & Mesiti P.C.; Victor A. Cardona, Esq.

(57) ABSTRACT

A compression force magnifier including a vertical axis through a body and a proximal surface of the body sloped at a predetermined angle relative to the vertical axis. A flat distal surface of the body is disposed opposite the proximal surface. A bore is disposed through the body from the proximal surface through the distal surface. The body is connected to an arm having a connection opening configured to allow connection of the body to a bone plate. The connection opening has a connection axis spaced from the vertical axis.

8 Claims, 31 Drawing Sheets

(56) References Cited

U.S. PATENT DOCUMENTS

| | | |
|---|---|---|
| 8,906,075 B2 | 12/2014 | Conley et al. |
| 9,204,912 B2 | 12/2015 | Price et al. |
| 9,414,870 B2 | 8/2016 | Ryan et al. |
| 9,572,607 B2 | 2/2017 | Johnson et al. |
| 9,681,896 B2 | 6/2017 | Aferzon |
| 10,076,377 B2 | 9/2018 | Bonutti et al. |
| 10,092,336 B2 | 10/2018 | Hess et al. |
| 10,111,693 B2 | 10/2018 | P et al. |
| 2004/0117016 A1 | 6/2004 | Abramson |
| 2005/0187551 A1 | 8/2005 | Orbay et al. |
| 2008/0015592 A1 | 1/2008 | Long et al. |
| 2012/0095466 A1 | 4/2012 | Winslow et al. |
| 2012/0116401 A1 | 5/2012 | Gradl et al. |
| 2012/0197301 A1 | 8/2012 | Foley et al. |
| 2014/0243828 A1 | 8/2014 | Heiney |
| 2015/0250509 A1* | 9/2015 | Kannan ............... A61B 17/8004 606/71 |
| 2016/0128745 A1 | 5/2016 | Sidebotham et al. |
| 2016/0228167 A1 | 8/2016 | Wahl |
| 2017/0156768 A1 | 6/2017 | Dresher et al. |
| 2018/0214163 A1 | 8/2018 | McCormick |
| 2019/0029739 A1 | 1/2019 | Finley |

\* cited by examiner

COMPRESSION FORCE MAGNIFIER

CROSS-REFERENCE TO RELATED APPLICATIONS

This application is related to U.S. patent application Ser. No. 15/978,071, entitled "Compression Force Magnifier", filed May 11, 2018, which claims the benefit of priority under 35 U.S.C. § 119 of U.S. Provisional Application, Ser. No. 62/505,418, filed on May 12, 2017, the entire disclosures of which are incorporated herein by reference.

BACKGROUND

Field of the Invention

The present invention relates generally to orthopedic implant fixation devices and, more particularly, to an orthopedic bone plate with a compression enhancement feature.

Description of the Related Art

Hal lux Abducto Valgus ("HAV") deformity is generally described as a medial deviation of the first metatarsal accompanied by a lateral deviation and/or valgus rotation of the hallux. The result effect is a subluxation of the first metatarsophalangeal joint ("MTPJ") creating a boney prominence on the inside of the foot near the base of the hallux. HAV may lead to painful motion of the hallux joint and/or difficulty fitting footwear. Other conditions associated with HAV may include: hammer toe formation of the adjacent toes, forefoot pain on the ball of the foot (aka metatarsalgia), stress fractures of the adjacent metatarsals, flat feet (pes planus), and arthritis. Misshaped bones (hallux and/or first metatarsal) may also cause bunions. Bunions have long been one of the more common types of painful foot deformities.

Various techniques have been developed to surgically correct HAV. The most basic technique simply involves resecting any enlarged bone at the medial aspect of the first metatarsal head, but this approach is typically used in conjunction with other more advanced techniques. A common technique involves an osteotomy (bone cut) procedure in which the first metatarsal is broken into two pieces and the distal portion of the bone is translated closer (medially) to the adjacent second metatarsal. The osteotomy may be performed at several locations on the first metatarsal depending on the severity of the deformity.

Alternative techniques have been developed that do not require an osteotomy. One such technique is often referred to as the Lapidus approach. In general, the idea behind the Lapidus approach is to permanently fuse the base of the first metatarsal to the medial cuneiform bone in a corrected new position. This permanent fixation is carried out by first reducing the IMA and then fusing the MC. Implementation of this approach often involves the use of a plate and screws that attach the plate to the metatarsal and medial cuneiform.

SUMMARY OF THE INVENTION

In one exemplary embodiment, the invention is a compression force magnifier comprising: an engaging surface for attaching to a bone plate; a ramped component above the engaging surface, the ramped component having a bottom surface adjacent the engaging surface and an angled upper surface; and a hole extending through the ramped component and the engaging surface.

In another exemplary embodiment, the invention is a compression force magnifier, said compression force magnifier comprising: a vertical axis; a proximal surface sloped at a predetermined angle relative to said vertical axis; a flat distal surface, said distal surface disposed opposite said proximal surface; an extension member, said extension member extending from said distal surface; a bore, said bore disposed through said body from said proximal surface through said distal surface and said extension member, said extension member adapted to fit into an aperture on a bone plate.

In another exemplary embodiment, the invention is a compression force magnifier, said compression force magnifier comprising: a vertical axis; a proximal surface sloped at a predetermined angle relative to said vertical axis; a flat distal surface, said distal surface disposed
   opposite said proximal surface; a bore, said bore disposed through said body from said proximal surface through said distal surface; and means for attaching said magnifier to a bone plate.

In another exemplary embodiment, the invention is a bone compression assembly apparatus, said assembly apparatus comprising: a bone plate, said plate having a proximal surface and a bone contacting surface disposed opposite said proximal surface, said bone plate further comprising at least one aperture disposed through said plate between said proximal surface and said bone contacting surface, said aperture having a longitudinal axis; and a compression force magnifier, said compression force magnifier disposed on the proximal surface of said bone plate, said compression force magnifier comprising: a vertical axis; a proximal surface sloped at a predetermined angle relative to said vertical axis; a flat distal surface, said distal surface disposed opposite said proximal surface; an extension member, said extension member extending from said distal surface; a bore, said bore disposed through said body from said proximal surface through said distal surface and said extension member, said extension member connected to said aperture on said bone plate such that the longitudinal axis of said aperture is generally colinear with the longitudinal axis of said bore.

In another exemplary embodiment, the invention is a bone compression assembly apparatus, said assembly apparatus comprising: a bone plate, said plate having a proximal surface and a bone contacting surface disposed opposite said proximal surface, said bone plate further comprising at least one aperture disposed through said plate between said proximal surface and said bone contacting surface, said aperture having a longitudinal axis; and a compression force magnifier, said compression force magnifier comprising: a vertical axis; a proximal surface sloped at a predetermined angle relative to said vertical axis; a flat distal surface, said distal surface disposed opposite said proximal surface; a bore, said bore disposed through said body from said proximal surface through said distal surface; said compression force magnifier attached to said bone plate such said axis of said bore is collinear with said axis of said aperture and said distal surface of said magnifier abuts said proximal surface of said plate.

In another exemplary embodiment, the invention is a bone compression assembly apparatus, said assembly apparatus comprising: a bone plate, said plate having a proximal surface and a bone contacting surface disposed opposite said proximal surface, said bone plate further comprising at least one aperture disposed through said plate between said proximal surface and said bone contacting surface, said aperture having a longitudinal axis; a compression force magnifier, said compression force magnifier comprising: a vertical axis; a proximal surface sloped at a predetermined angle relative to said vertical axis; a flat distal surface, said distal surface disposed opposite said proximal surface; a bore, said bore disposed through said body from said proximal surface through said distal surface; said compression force magnifier attached to said bone plate such said axis of said bore is collinear with said axis of said aperture and said distal surface of said magnifier abuts said proximal surface of said plate; and a screw, said screw having a proximal head having a non-flat bottom, said screw disposed through said bore and said aperture and into a bone.

In another exemplary embodiment, the invention is a bone plate, said plate comprising: an elongated body, said body having a proximal non-bone contacting surface and a distal bone contacting surface disposed opposite said proximal surface; an aperture disposed through said plate, said aperture in communication with said proximal surface and said distal surface of said plate, said aperture comprising a vertical axis; and a compression magnification element, said compression magnification element having a vertical axis, a proximal surface sloped at a predetermined angle relative to said vertical axis, a flat distal surface disposed opposite said proximal surface, and a bore disposed through said compression magnification element from said proximal surface through said distal surface, said compression magnification element disposed on said plate such that said vertical axis of said bore for said compression magnification element is colinear with said vertical axis of said aperture of said plate.

In another exemplary embodiment, the invention is a bone plate, said plate comprising: an elongated body, said body having a first end, a second end, a proximal non-bone contacting surface, and a distal bone contacting surface disposed opposite said proximal surface; an aperture disposed through said plate, said aperture in communication with said proximal surface and said distal surface of said plate, said aperture comprising a vertical axis; and a compression magnification element, said compression magnification element having a vertical axis, a proximal surface sloped at a predetermined angle relative to said vertical axis, a flat distal surface disposed opposite said proximal surface, and a bore disposed through said compression magnification element from said proximal surface through said distal surface, said compression magnification element attached to one of said first and second end of said plate.

In another exemplary embodiment, the invention is a bone compression assembly comprising: a bone plate including a plurality of screw holes; and a compression force magnifier engaged within at least one screw hole, the compression force magnifier comprising: an engaging surface for attaching to a bone plate; a ramped component above the engaging surface, the ramped component having a bottom surface adjacent the engaging surface and an angled upper surface; and a hole extending vertically through the ramped component and the engaging surface.

In another exemplary embodiment, the invention is a method of using a compression force magnifier, the method comprising: attaching a bone plate to a first bone; inserting a compression force magnifier into an opening disposed on a top surface of the bone plate; inserting a first screw into the compression force magnifier and into a second bone; applying a compressive force between the first bone and the second bone; inserting a second screw through a hole in the bone plate into the second bone; removing the first screw and the compression force magnifier; and inserting a third screw, larger than the first screw, into a hole left by the first screw.

BRIEF DESCRIPTION OF THE DRAWINGS

For the purposes of illustrating the compression bone plate apparatus and related methods described herein, there is shown herein illustrative embodiments. These illustrative embodiments are in no way limiting in terms of the precise arrangement and operation of the disclosed compression bone plate apparatus and related methods and other similar embodiments are envisioned within the spirit and scope of the present disclosure.

DETAILED DESCRIPTION

Figure 1:
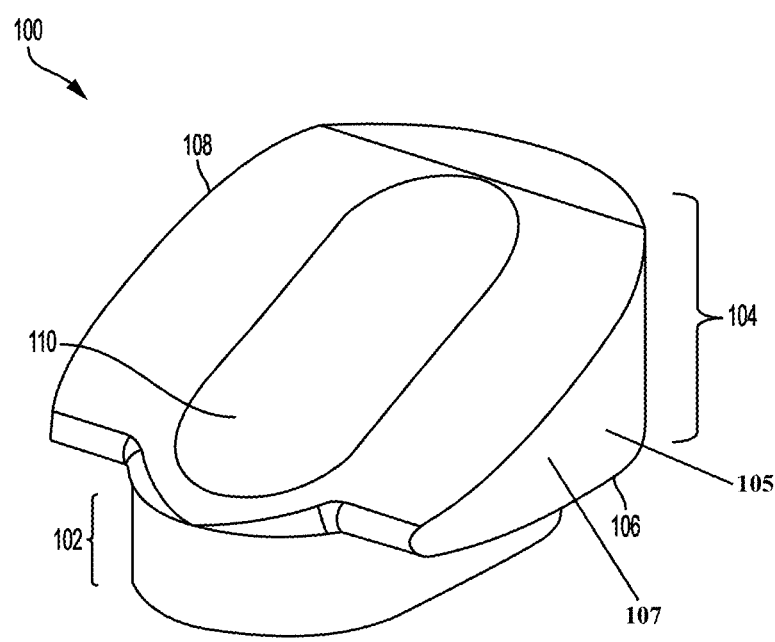
FIG. 1 illustrates a top perspective view of a compression force magnifier, in accordance with an aspect of the present invention.

The term "compression force magnifier" as used herein shall not be interpreted as limited to use on any particular joint, but the phrase may be used for fusion and osteotomy of any type of joint, and further may be used to reduce a joint prior to soft tissue repair.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

As shown in FIGS. 1-5, the embodiments of compression force magnifiers, according to the present disclosure, are disclosed. The compression force magnifier 100 can include an engaging surface 102 for mating with a bone plate, as will be described and illustrated later. The engaging surface 102 can include any means for attaching to, for instance, a screw hole in a bone plate. This can include, for example, but is not limited to an interference tab, which is compressed when inserted into a slot, an interference fit between a screw slot and hole, a tapered fit, a press-fit, a tab for engaging a ridge in a screw slot, or a split bottom which engages the screw slot and causes essentially a friction fit.

As shown in FIGS. 1-5, the compression force magnifier 100 may also include a ramped component 104 positioned above the engaging surface 102. For instance, the ramped component 104 may include a flat bottom surface 106 immediately adjacent to the engaging surface 102 for sitting against a surface of a bone plate. As shown in FIGS. 1-4, the ramped component may also include a pitched, or angled, upper surface 108, creating a ramped surface, the angle of which may vary for example from 1 to 89 degrees, but more preferably in the range of 20 to 55 degrees with a height range for example of generally 1.5 to 5 millimeter. Sides 105 of ramped component 104 may connect flat bottom surface 106 and upper surface 108 to form a body 107 thereof.

Figure 2:
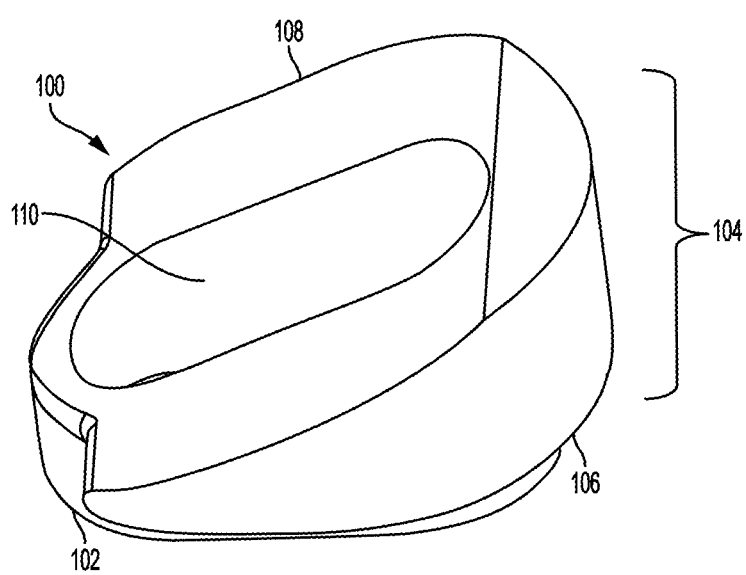
FIG. 2 illustrates a side perspective view of a compression force magnifier in accordance with an aspect of the present invention.
Figure 3:
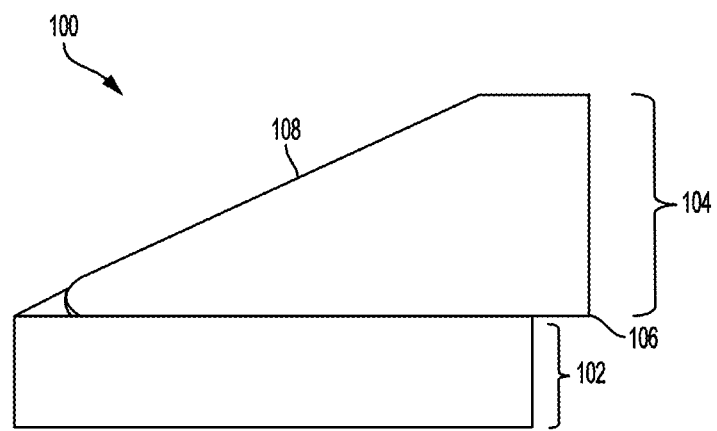
FIG. 3 illustrates a side elevational view of a compression force magnifier, in accordance with an aspect of the present invention.
Figure 4:
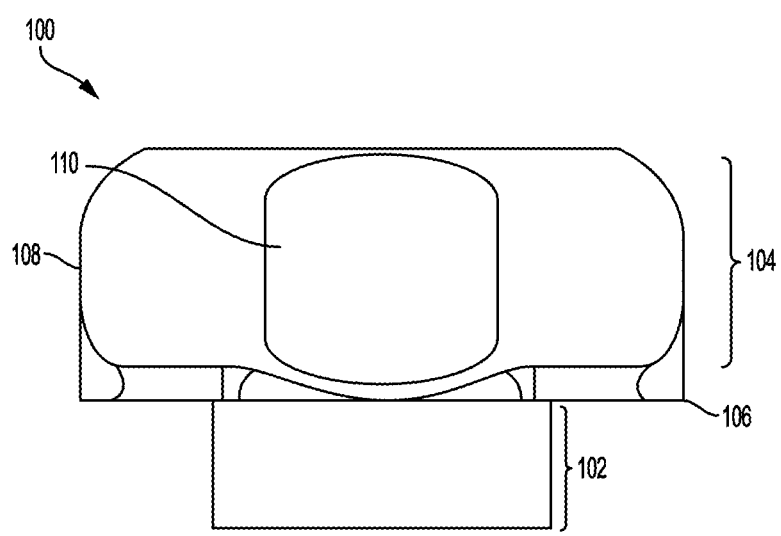
FIG. 4 illustrates a front elevational view of a compression force magnifier, in accordance with an aspect of the present invention.
Figure 5:
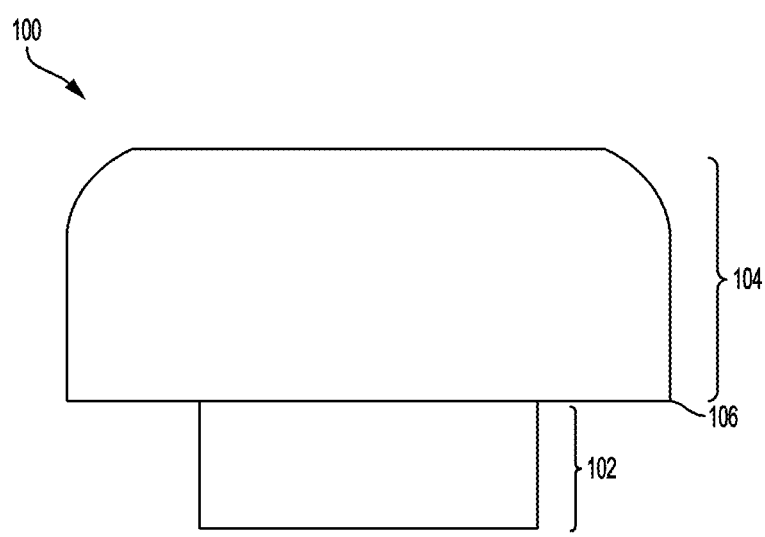
FIG. 5 illustrates a rear elevational view of a compression force magnifier, in accordance with an aspect of the present invention.
Figure 6:
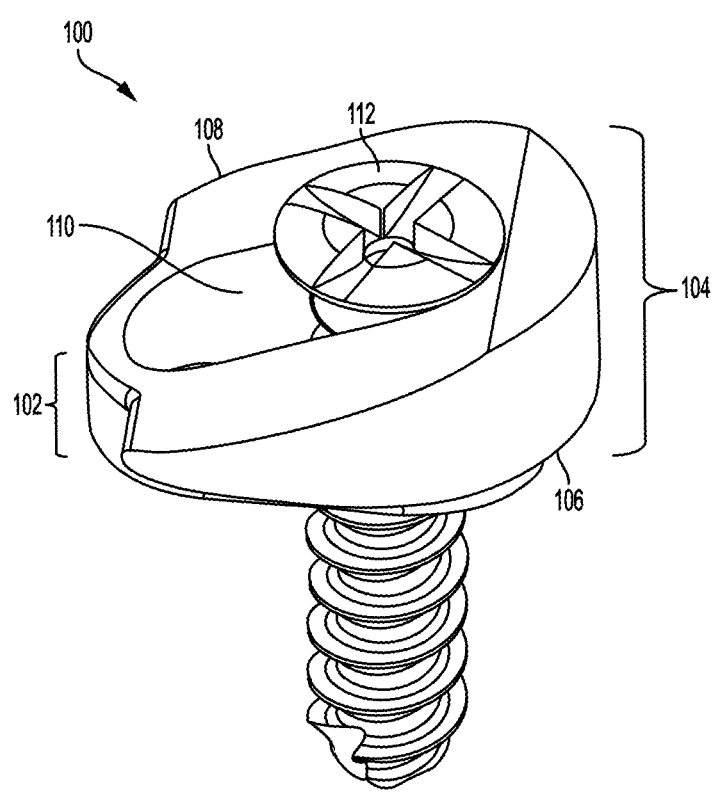
FIG. 6 illustrates a side perspective view of a compression force magnifier with an inserted screw, in accordance with an aspect of the present invention.
Figure 7:
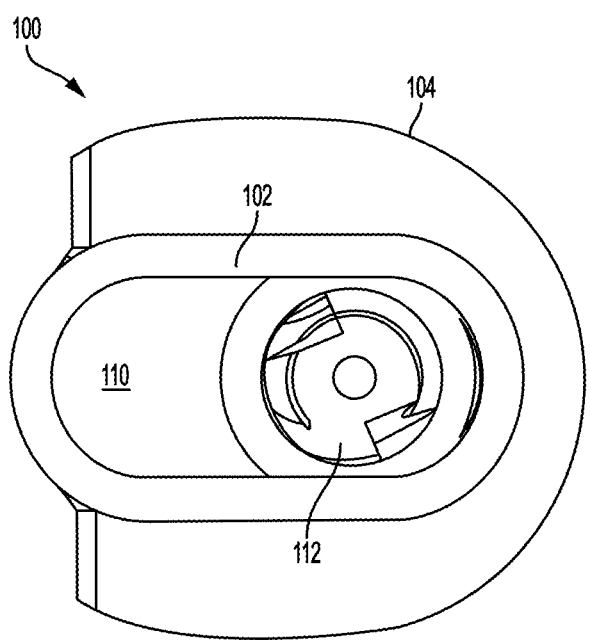
FIG. 7 illustrates a bottom view of a compression force magnifier with an inserted screw, in accordance with an aspect of the present invention.
Figure 8:
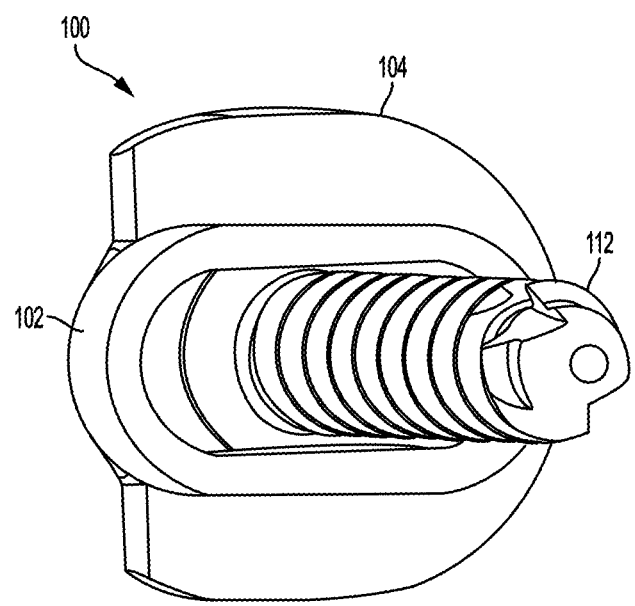
FIG. 8 illustrates a bottom perspective view of a compression force magnifier with an inserted screw, in accordance with an aspect of the present invention.
Figure 9:
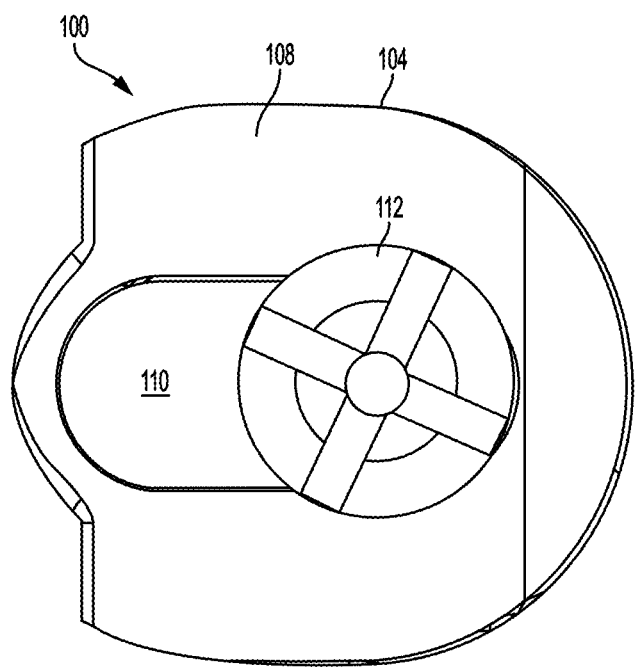
FIG. 9 illustrates a top view of a compression force magnifier with an inserted screw.
Figure 10:
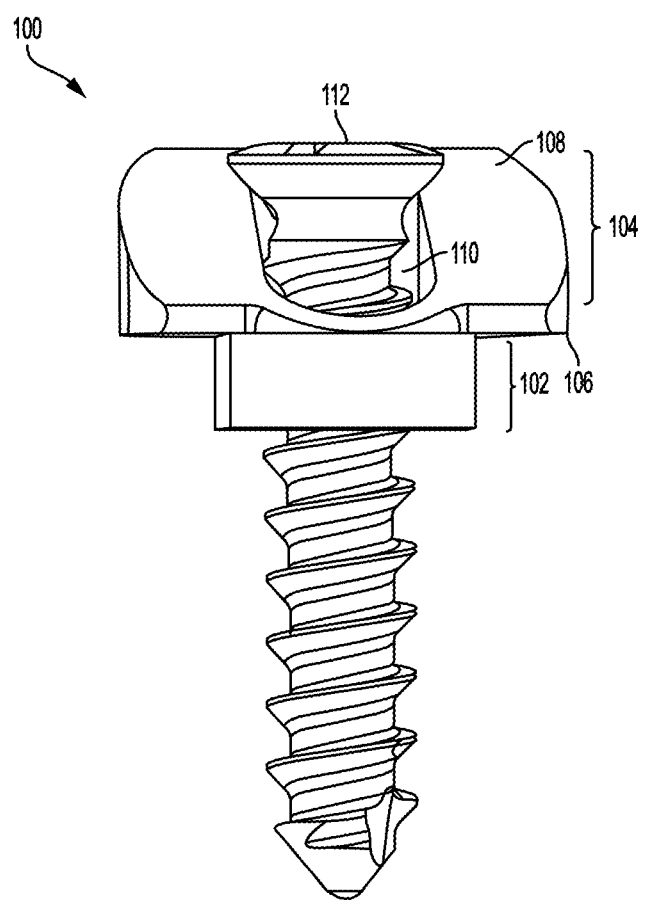
FIG. 10 illustrates a front elevational view of a compression force magnifier with an inserted screw, in accordance with an aspect of the present invention.
Figure 11:
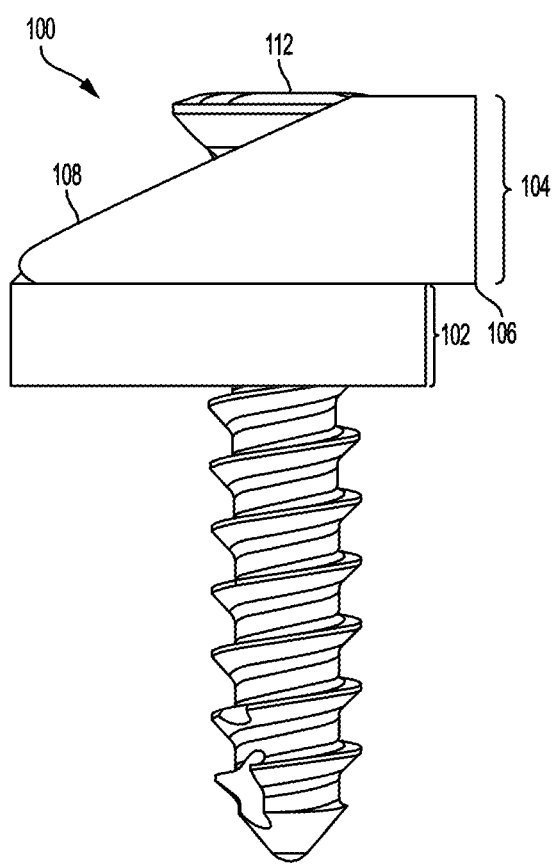
FIG. 11 illustrates a side elevational view of a compression force magnifier with an inserted screw, in accordance with an aspect of the present invention.
Figure 12:
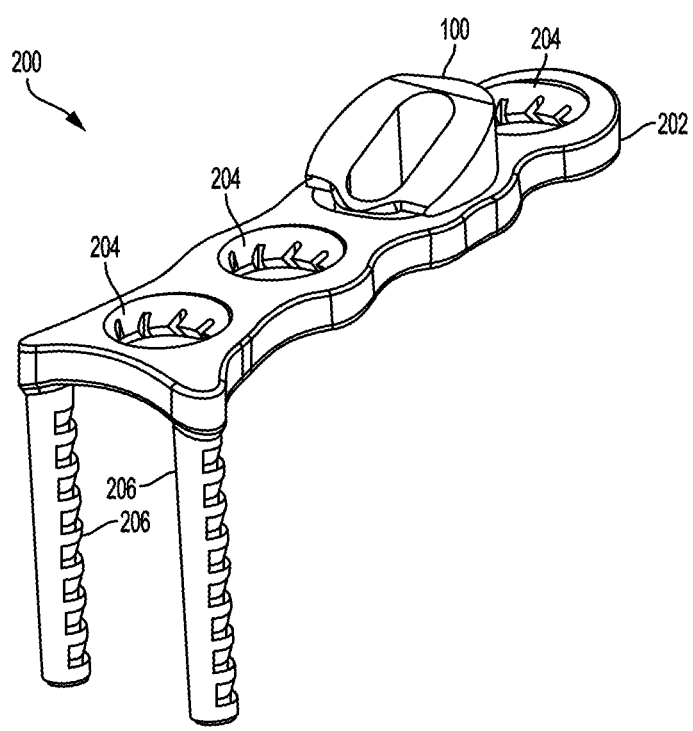
FIG. 12 illustrates a top perspective view of a compression bone plate with an inserted force magnifier, in accordance with an aspect of the present invention.
Figure 13:
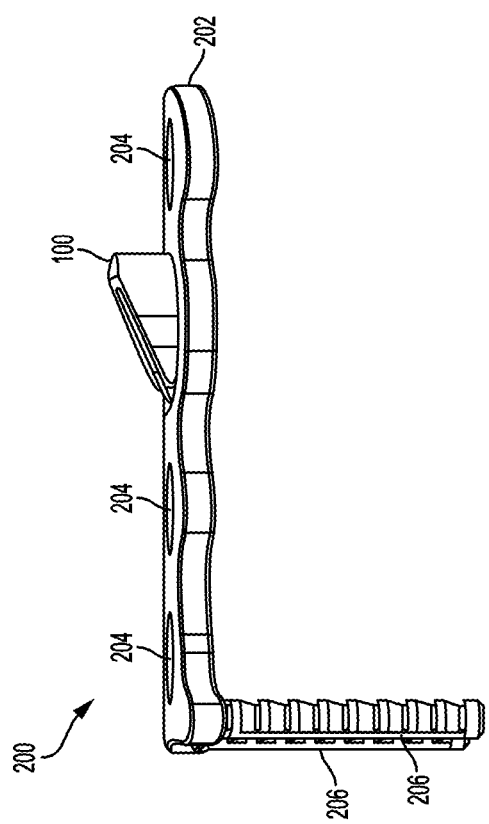
FIG. 13 illustrates a side elevational view of a compression bone plate with an inserted force magnifier, in accordance with an aspect of the present invention.

As shown in FIGS. 1, 2 and 4, the compression force magnifier 100 can include a bore or hole 110 extending vertically through walls forming a body of the ramped component 104 and the engaging surface 102 so that an opening extends through the entirety of the compression force magnifier 100. The hole 110, for example, may be an oval shape, defining for example, a slot. As seen in FIG. 6, as a screw is tightened into a bone that sits below a base plate, the screw will translate or move down the ramped component 104 and across the slot, to create a high compressive force through the bone plate, as will be explained in more detail below. Hole 110 may include an axis along a centerline thereof extending through the body, and such axis may be vertical when engaging surface is oriented horizontally as shown for example in FIGS. 4 and 5.

As shown in FIGS. 6-11, the compression force magnifier 100 may be used in conjunction with a threaded device, such as for example, a screw 112 or k-wire (not shown), for attaching to a bone or bone fragment positioned below the coupled bone plate. For instance, when the screw 112 is inserted through the hole 110 at the top of the ramped component 104, as the screw 112 is tightened into the underlying bone, the screw will migrate or move down the ramped component 104, causing the bone to move in a direction parallel to the length of the slot, in some instances drawing one bone closer to another bone or bone fragment through the compressive force applied as the screw descends the ramp. The movement of the screw will draw two bones closer together, but will also apply a larger compressive force by virtue of the height of the ramp and resultant higher created leverage force.

Figure 14:
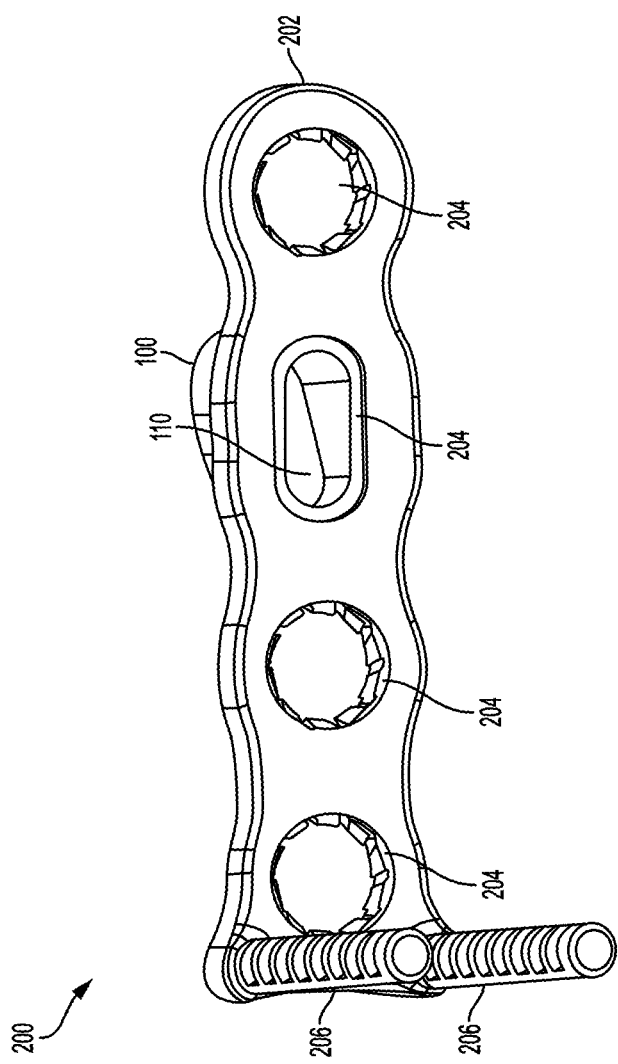
FIG. 14 illustrates a bottom perspective view of a compression bone plate with an inserted force magnifier, in accordance with an aspect of the present invention.
Figure 15:
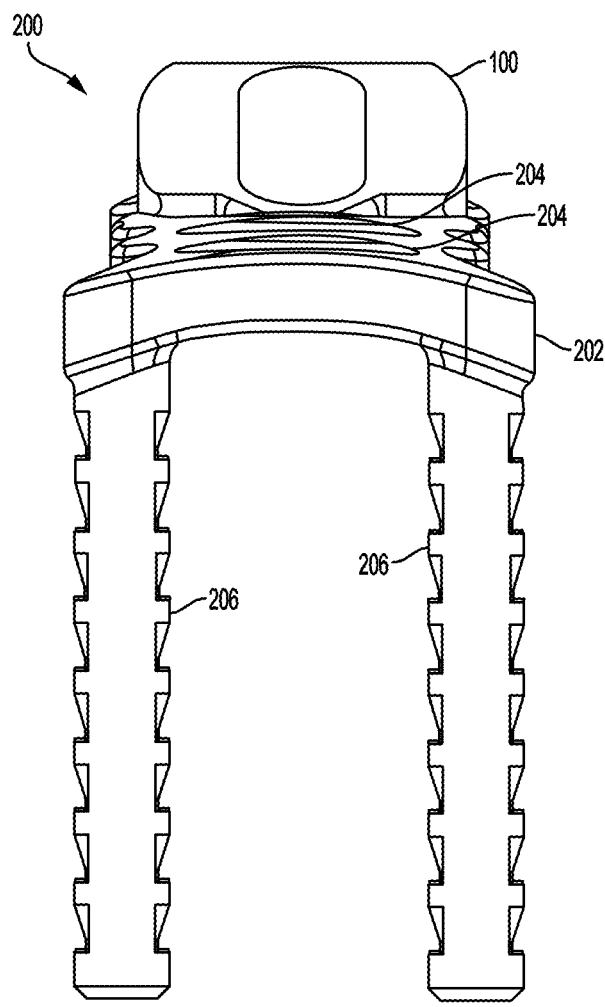
FIG. 15 illustrates a front elevational view of a compression bone plate with an inserted force magnifier, in accordance with an aspect of the present invention.

As shown in FIGS. 12-15, also disclosed is a bone compression assembly 200, which may include for example, a bone plate 202. The bone plate 202 as shown may be an elongate bone plate with a slight medial-lateral curvature as illustrated in FIGS. 12-15, but it can also include step bone plates or other orthogonal designs. The bone plate 202 can include a plurality of screw holes 204 for attaching the bone plate 202 to one or more bones or bone fragments (not shown). Additionally, a set of tines 206, for example, may be included on the bone plate 202 for implantation in a bone or bone fragment. The compression force magnifier 100, as described previously, may be inserted or nested into at least one screw hole 204, and as seen in FIG. 14, the particular screw hole 204 may be configured as a slot to match the engagement surface 102 of the compression force magnifier 100.

Figure 16:
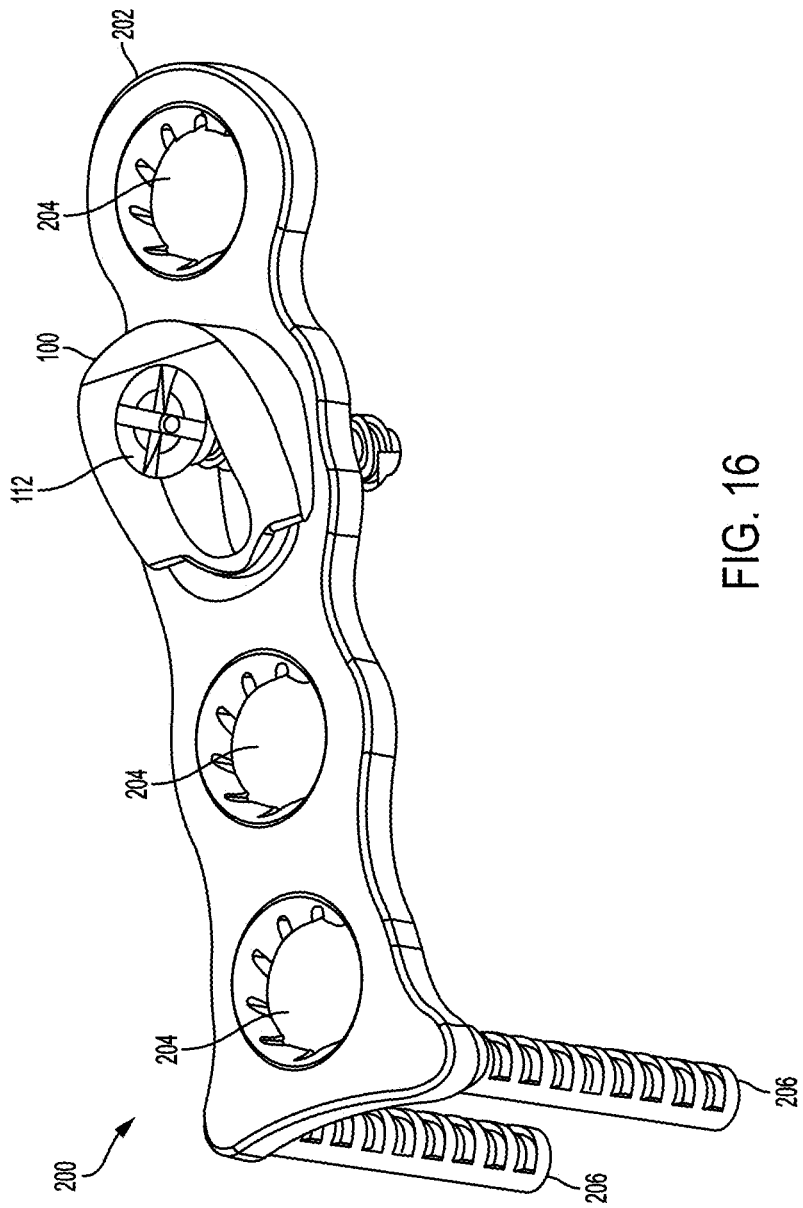
FIG. 16 illustrates a side perspective view of a compression bone plate with an inserted force magnifier and inserted compression screw, in accordance with an aspect of the present invention.
Figure 17:
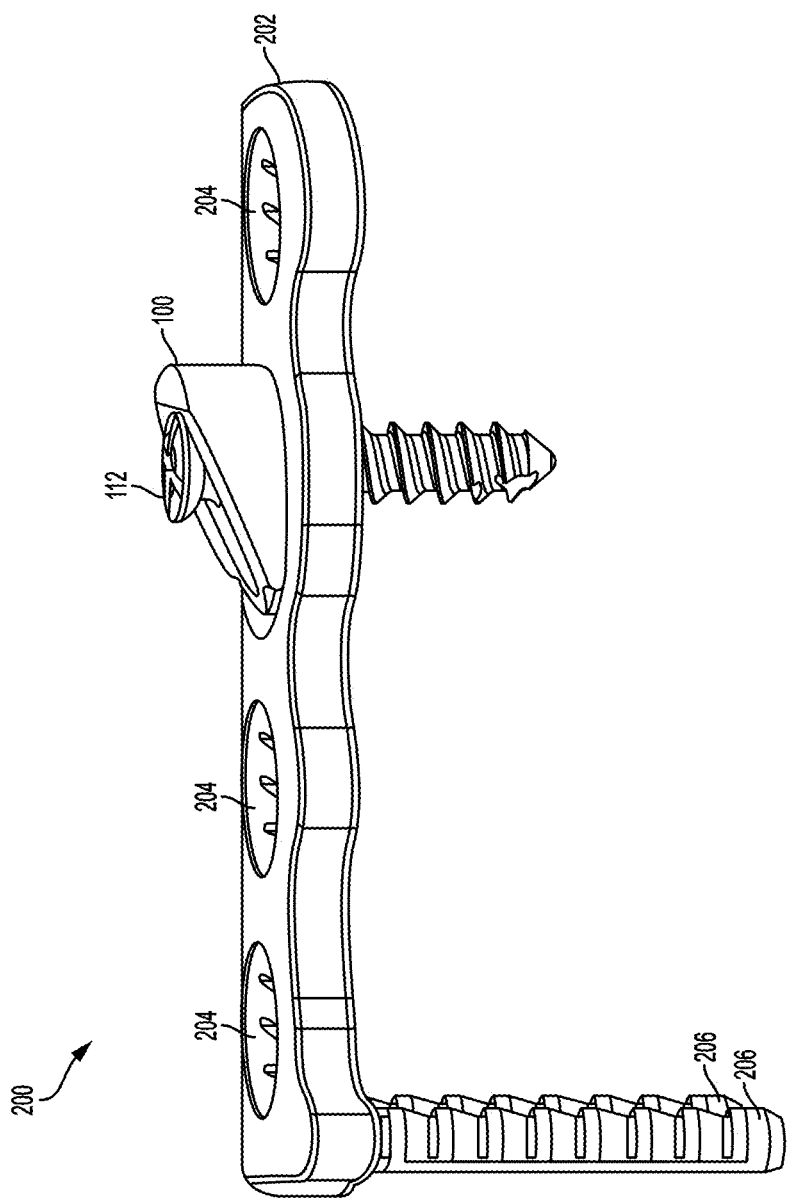
FIG. 17 illustrates a side elevational view of a compression bone plate with an inserted force magnifier and inserted screw, in accordance with an aspect of the present invention.

As seen in FIGS. 16 and 17, similar to FIGS. 6-11, a screw 112 may be used in conjunction with the bone compression assembly 200, to facilitate the movement of two bones and/or fragments closer together. When the screw 112 inserted, it moves down the ramp in the direction indicated by the arrows of FIGS. 16 and 17, moving the second bone a distance D, which may be equal to the length of the slot of hole 110, which pulls the bone and/or fragment below the bone plate 202 closer to a second bone and/or fragment, which is secured to the bone plate 202.

The method, more specifically, of using a bone compression assembly 200 includes attaching a bone plate 202 to a first bone or fragment, for instance on the left side of FIG. 17, using tines 206 or screws or other bone fixation devices, such as compression screws or locking screws, through at least one of the screw holes 204 on the left side of the assembly 200. A compression force magnifier 100 may, before or after attaching the bone plate 202 to a first bone or fragment, be inserted into at least one of the screw holes 204 of the bone plate 202. A first screw 112 may be inserted into and through the compression force magnifier 100 (e.g., through hole 110) and into a second bone or fragment, for instance, on the right side of the assembly 200. Tightening of the first screw 112 results in a compressive force being applied between the first bone or fragment and the second bone or fragment, as described above. As the screw 112 moves down the ramp the resultant force pulls the second bone on the right side toward the left side of the assembly 200, closer to or into contact with the first bone on the left side of the assembly 200. Any amount of pressure may be applied by continuing to tighten the screw 112 to the end of the ramped surface 108 of the compression force magnifier 100. When the desired amount of movement has been achieved, the bone plate may be more permanently attached to the second bone or fragment, for instance, by inserting a second screw, such as a compression screw or locking screw, into the right most screw hole 204 of the bone plate 202.

Once the second bone or fragment is secured to the bone plate 202, the first screw 112 may be unscrewed and removed, with the bones positions remaining where they were. The compression force magnifier 100 may then be removed utilizing any tool or method necessary to disengage the engaging surface 102 of the compression force magnifier 100. While illustrated with four screw holes 204, the bone plate 202 may include any number of holes, and all or some may be used for securing the bone plate 202 to the first and second bones or bone fragments, depending on the type of joint compression necessary and the size and strength of the bones. Once all of the screw holes to be used have been filled with screws or other fixation devices, the compression force magnifier 100 is removed, and the remaining screw hole, which may be slotted (e.g., be oval shaped or otherwise have a longitudinal dimension larger than a transverse dimension to allow relative movement of the screw therein), can be utilized to help further secure the second bone by inserting a third screw or other fixation device, which may have a larger diameter than the first screw, into the hole left in the bone by the first screw 112. For example, the first screw 112 may create a pilot hole for the final screw, which will fit flush in the remaining screw hole/slot. Having the removable compression force magnifier 100, eliminates the clinical problem of resultant proud or protruding screws, which may have happened with previous designs of compression devices which include integrated ramps rather than a removable device as in compression force magnifier 100. In some embodiments, the initial first screw may be between 1 and 2 mm, and the subsequent second screw may be in the range of between 2 and 6.5 mm. The ramp angle and length of the compression force magnifier 100 allows for movement or a translational distance of the second bone/fragment in the range of 1 and 5 mm.

Figure 18:
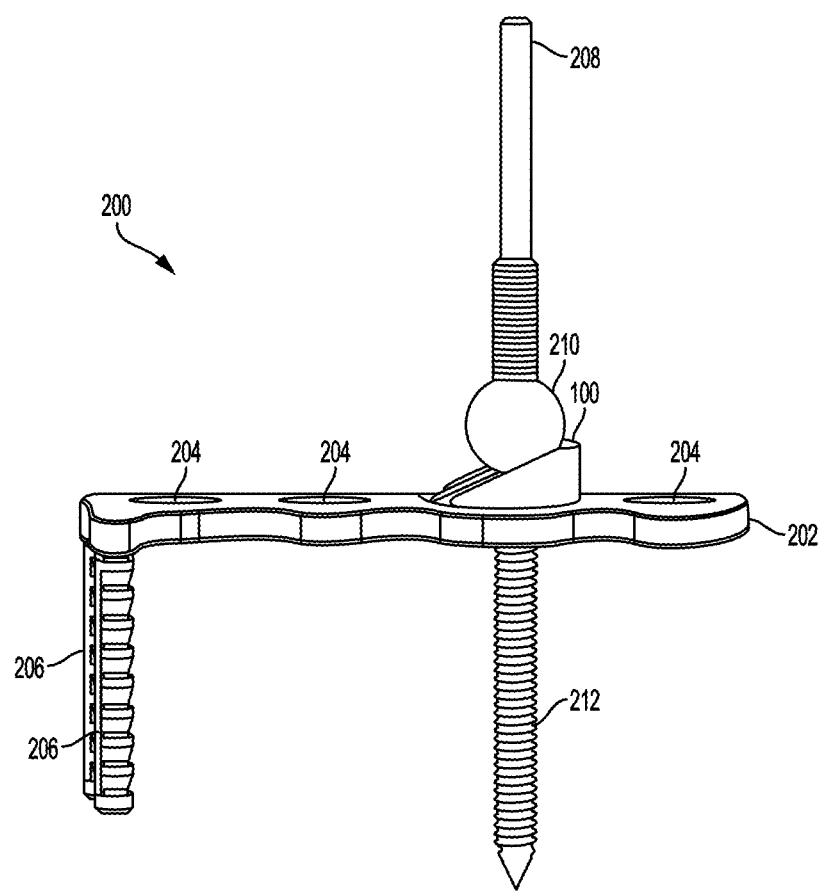
FIG. 18 illustrates a side elevational view of a compression bone plate with an inserted force magnifier and an inserted olive wire, in accordance with an aspect of the present invention.
Figure 19:
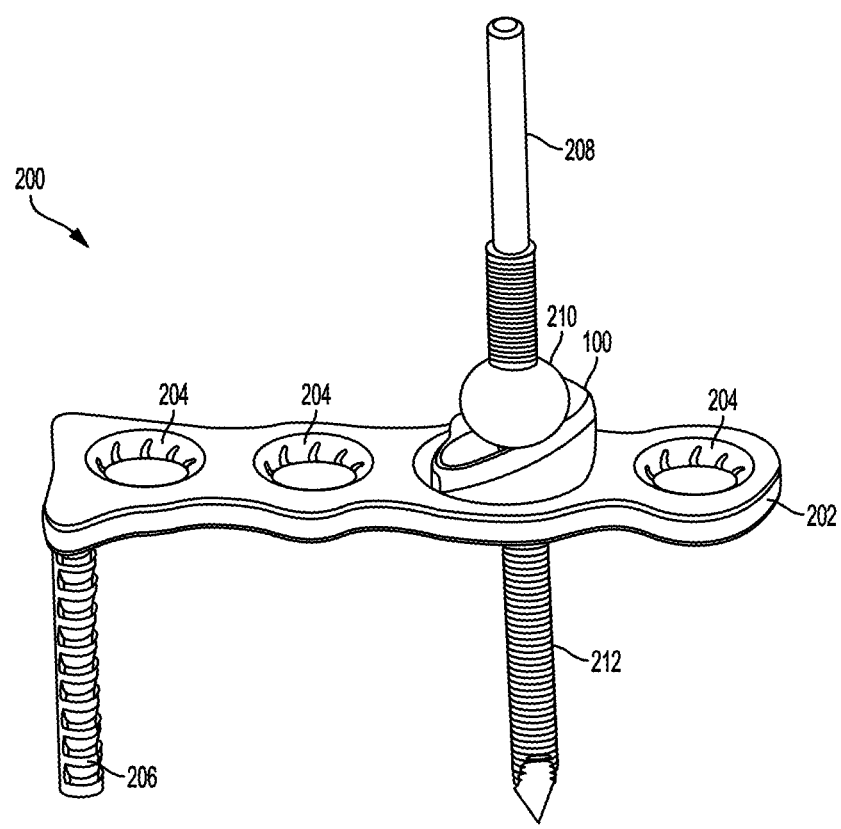
FIG. 19 illustrates a side perspective view of a compression bone plate with an inserted force magnifier and an inserted olive wire, in accordance with an aspect of the present invention.

Although a screw 112 is described as being used in the screw hole 110 of the compression force magnifier 100, in an alternative embodiment, as illustrated in FIGS. 18-19, a threaded olive wire 208 may be utilized, including a ball 210 as opposed to the head of a screw, to translate down the ramped surface. Any olive wires known in the art may be used, and it may include a cancellous screw thread or other compression screw thread 212 on the bottom end of the wire, which like the screw above, may be a smaller diameter than the end screw which will be inserted.

Figure 20:
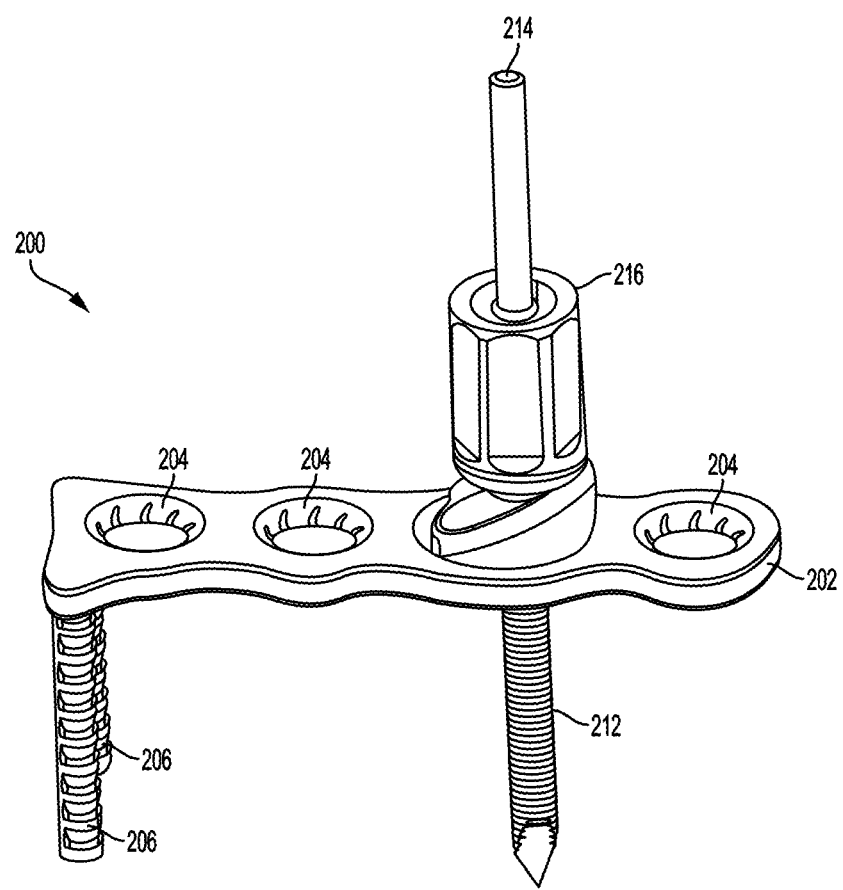
FIG. 20 illustrates a side perspective view of a compression bone plate with an inserted force magnifier and an inserted threaded pin with an engaged nut, in accordance with an aspect of the present invention.

Further, shown in FIG. 20 is another alternative embodiment to the screw 112, which may include a threaded pin 214 including a cancellous screw thread or other compression screw thread 212 on the bottom end of the pin 214. A nut 216 or similar threaded member may be utilized to engage the threaded top portion of pin 214. The nut 216 would migrate down the ramp of the compression force magnifier 100 as it is threaded onto the threaded pin, to create and apply the compression force between the two bones.

Figure 21:
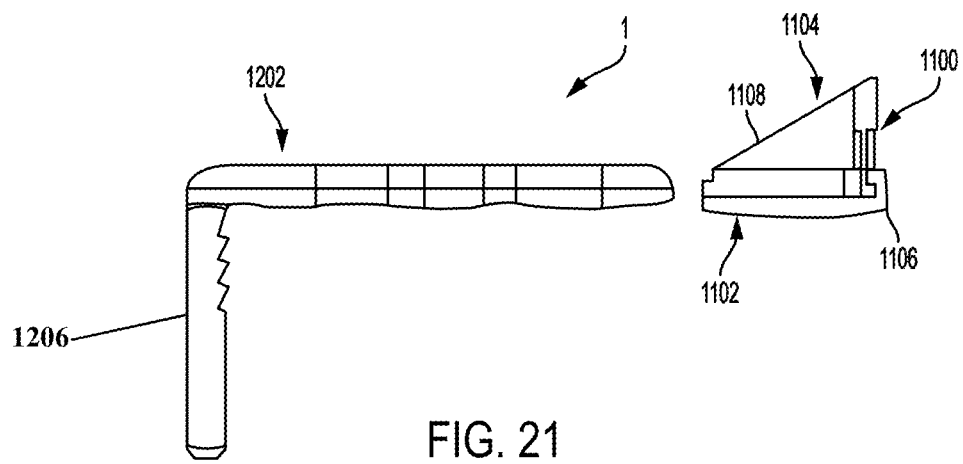
FIG. 21 illustrates a side disassembled view of an alternative embodiment of a compression bone plate with a force magnifier in accordance with an aspect of the present invention.
Figure 22:
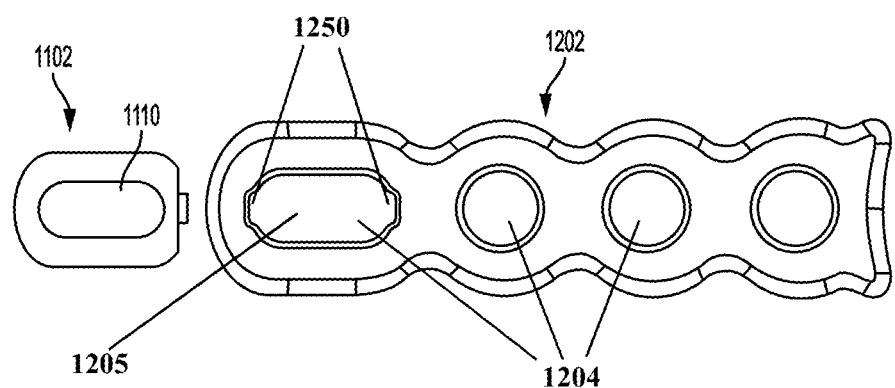
FIG. 22 illustrates a top disassembled view of an alternative embodiment of a compression bone plate with a force magnifier in accordance with an aspect of the present invention.
Figure 23:
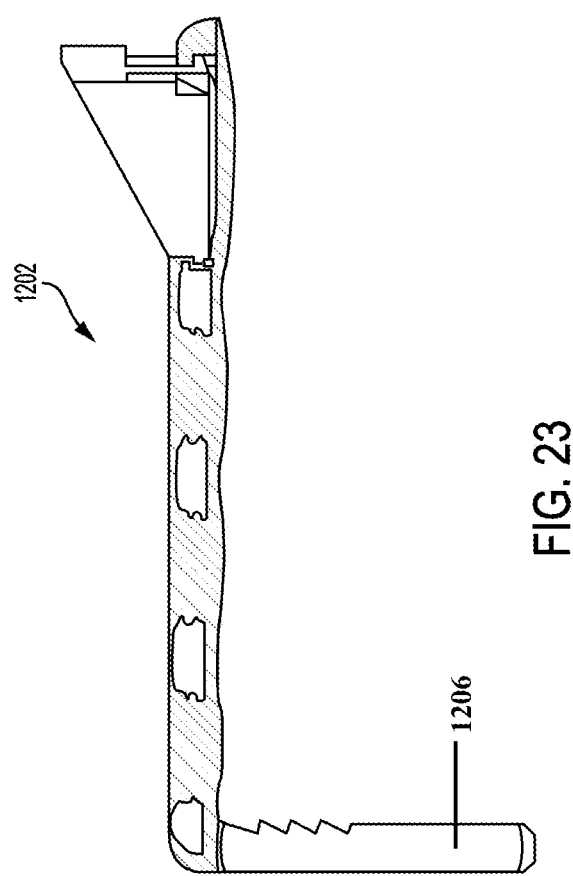
FIG. 23 illustrates a side assembled view of an alternative embodiment of a compression bone plate with a force magnifier in accordance with an aspect of the present invention.

FIGS. 21-23 illustrate a side disassembled view, a top disassembled view, and a side assembled view, respectively of an alternative embodiment of a compression bone plate 1202 with a force magnifier 1100. As shown in FIGS. 21-23, the compression force magnifier 1100 may also include a ramped component 1104 positioned above the engaging surface 1102. For instance, the ramped component 1104 may include a flat bottom surface 1106 immediately adjacent to the engaging surface 1102 for sitting against a surface of a bone plate. The ramped component may also include a pitched, or angled, upper surface 1108, creating a ramped surface, the angle of which may vary for example from 1 to 89 degrees, but more preferably in the range of 20 to 55 degrees with a height range for example of generally 1.5 to 5 millimeters.

As shown in FIGS. 21-23, the compression force magnifier 1100 can include a hole 1110 extending vertically through the ramped component 1104 and the engaging surface 1102 so that an opening extends through the entirety of the compression force magnifier 1100. The hole 1110, for example, may be an oval shape, defining for example, a slot.

In the same manner shown in FIG. 6, as a screw is tightened into a bone that sits below a base plate, the screw will translate or move down the ramped component 1104 and across the slot, to create a high compressive force through the bone plate, as will be explained in more detail below.

As shown in FIG. 23, bone compression assembly 1200 includes bone plate 1202. The bone plate 1202 as shown may be an elongated bone plate with a slight medial-lateral curvature as illustrated in FIGS. 12-15 relative to bone plate 202, but it can also include step bone plates or other orthogonal designs. The bone plate 1202 can include a plurality of screw holes 1204 for attaching the bone plate 1202 to one or more bones or bone fragments (not shown). Additionally, a set of tines 1206, for example, may be included on the bone plate 1202 for implantation in a bone or bone fragment.

The compression force magnifier 1100, as described previously, may be inserted or nested into at least one screw hole of screw holes 1204, and as seen in FIGS. 21-22, a particular screw hole (e.g., a hole 1205) of screw holes 1204 may be configured with cutouts 1250 to match corresponding flexible tabs on compression force magnifier 1100 as an alternative means for connecting the two components. For example, cutouts 1250 may be narrowed portions extending longitudinally relative to the bone plate from a remainder of one of holes 1204. Such tabs may extend in a direction of a longitudinal dimension of bone plate 102 longer than the cutouts extend longitudinally, and the tabs may be elastically deformable to allow the tabs to deform longitudinally to pass through cutouts 1250 of hole 1205. After being deformed and passing through cutouts 1250 of hole 1205 the tabs may extend longitudinally such that the tabs are located on an opposite side of the bone plate relative to a remainder of compression force magnifier 100 to inhibit a separation of the compression force magnifier from the bone plate. In another example, the tabs may frictionally fit in cutouts 1250 to inhibit such separation without extending on the opposite side of the bone plate relative to the remainder of compression force magnifier 100.

Figure 24:
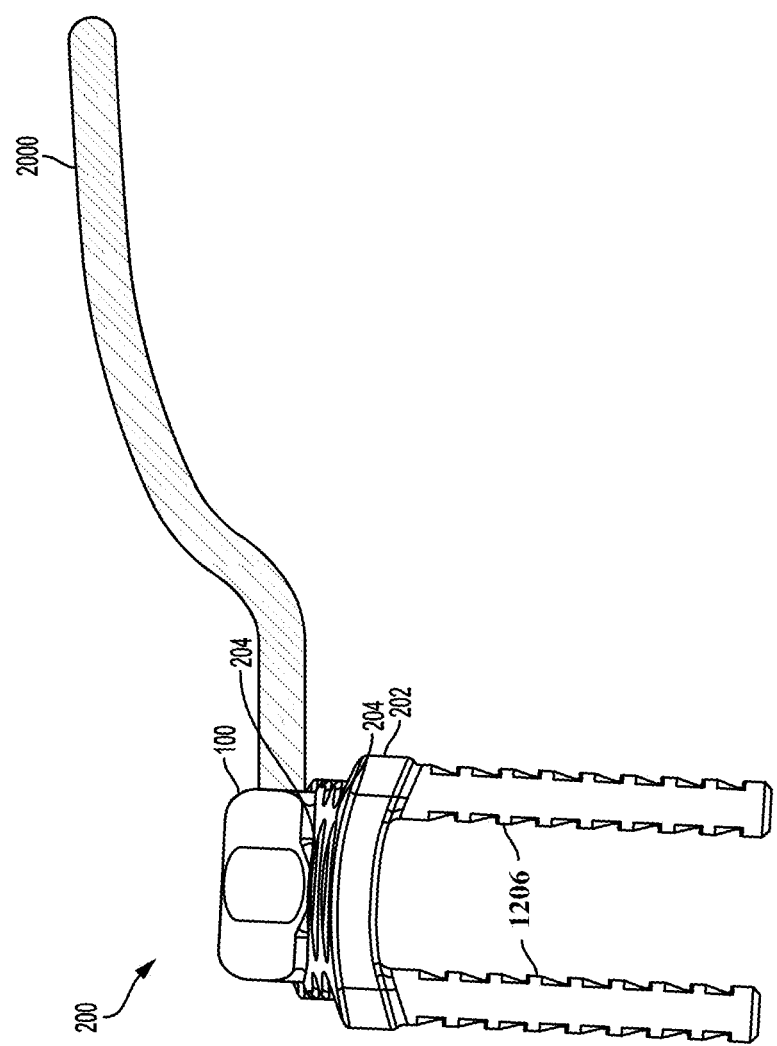
FIG. 24 illustrates a top view of a handle for use as a force magnifier for a compression bone plate in accordance with an aspect of the present invention.
Figure 25:
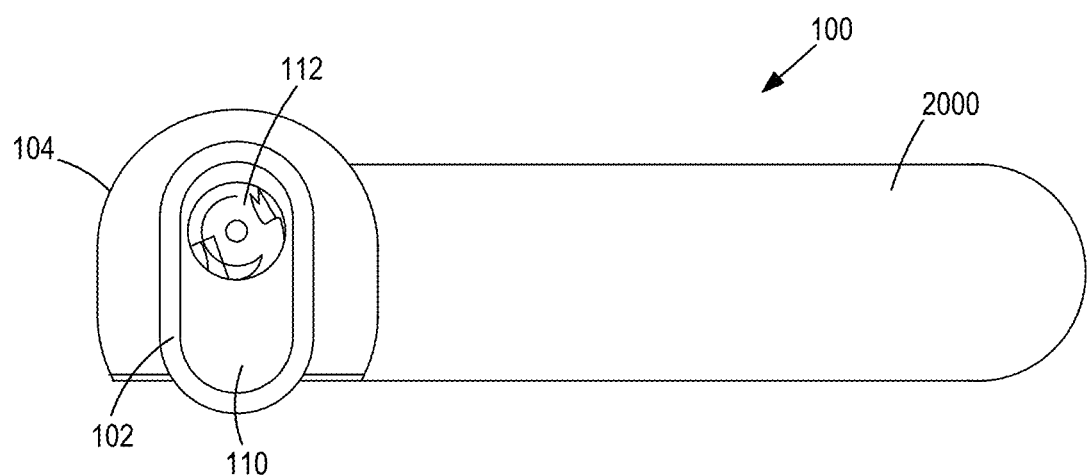
FIG. 25 illustrates a top view of a handle for use as a force magnifier for a compression bone plate in accordance with an aspect of the present invention.

FIGS. 24 and 25 illustrate a side and top view respectively of a handle 2000 for use as a force magnifier for a compression bone plate in accordance with an aspect of the present invention. As illustrated in FIGS. 24 and 25, handle 2000 may incorporate the features of compression force magnifier 100 or 1100 to provide addition compression to a bone plate 202 or 1202.

Figure 26:
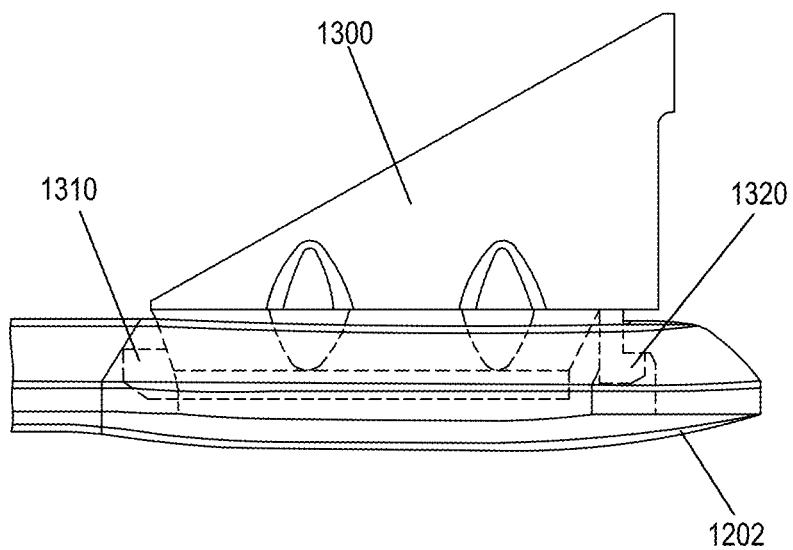
FIG. 26 is a side view of a compression force magnifier received in a bone plate with the bone plate being transparent to show tabs of the compression force magnifier coupled to the bone plate in accordance with an aspect of the present invention.
Figure 27:
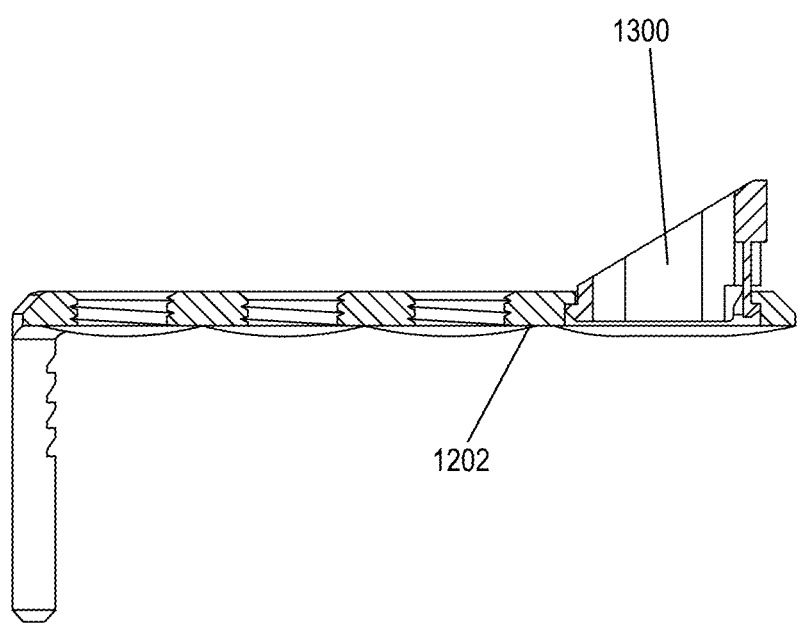
FIG. 27 is a side view of the compression force magnifier of FIG. 26 received in the bone plate.
Figure 28:
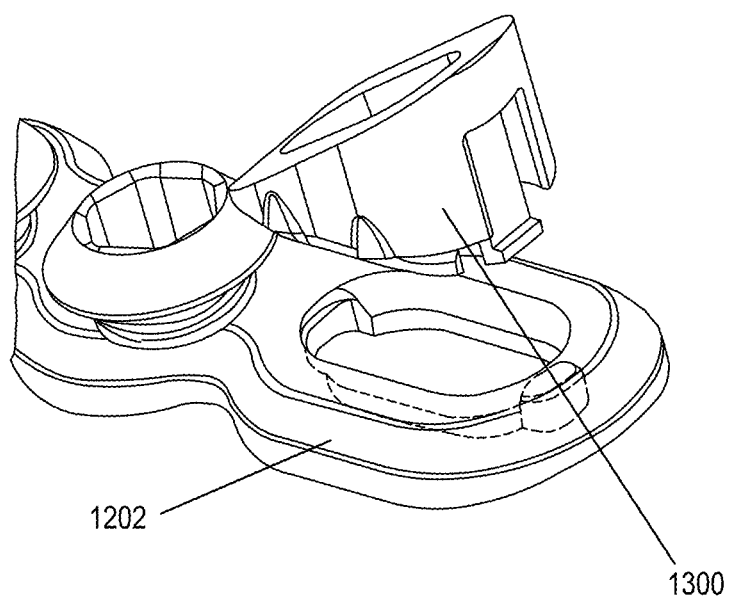
FIG. 28 is a perspective view of the compression force magnifier and a portion of the bone plate of FIG. 27 in an exploded view with the compression force magnifier separated from the bone plate.
Figure 29:
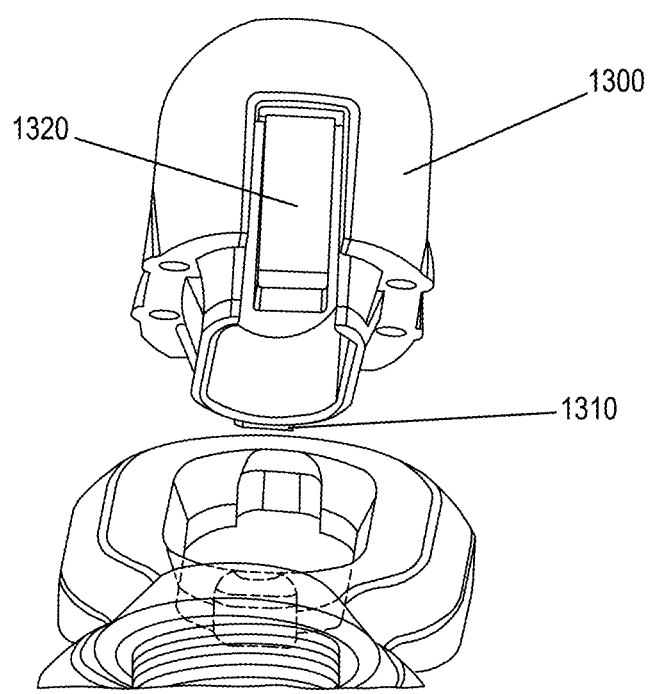
FIG. 29 is another perspective view of the compression force magnifier of FIG. 28 separated from the bone plate.
Figure 30:
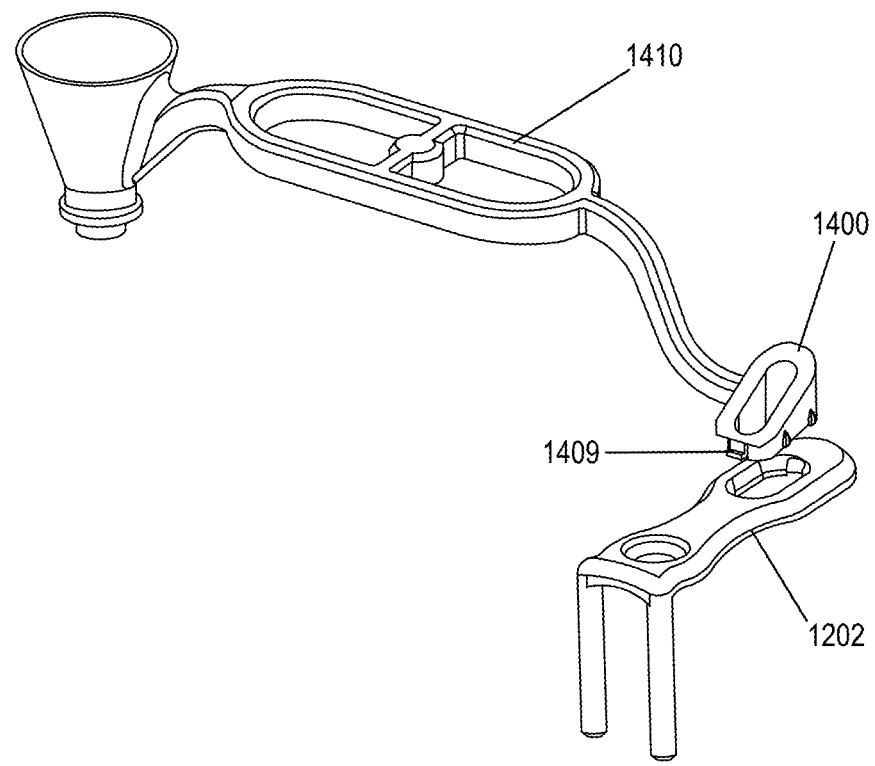
FIG. 30 is a perspective view of a compression force magnifier having a handle connectable to, and separated from, a bone plate in accordance with an aspect of the present invention.
Figure 31:
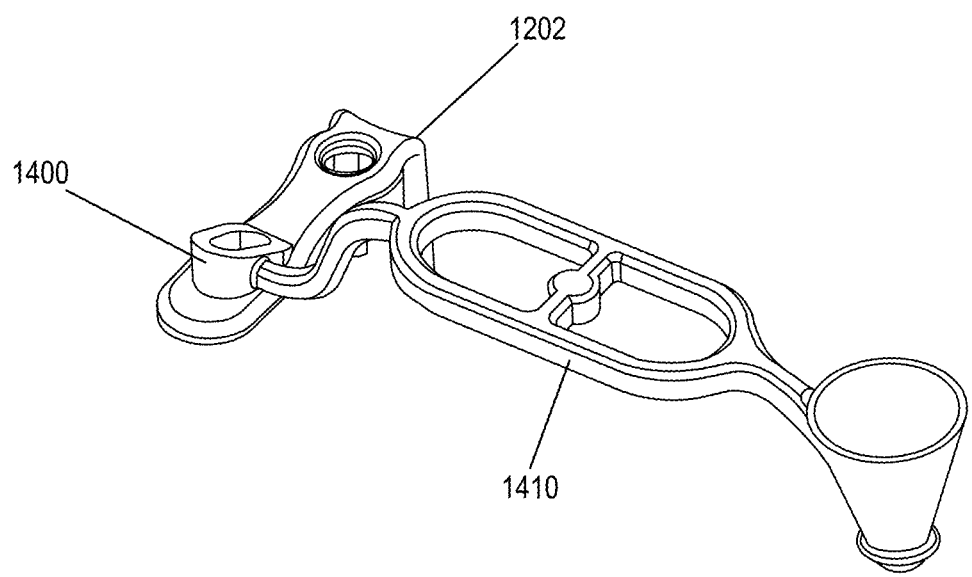
FIG. 31 is a perspective view of the bone plate and compression force magnifier of FIG. 30 received in a cavity of the bone plate.

In another example depicted in FIGS. 26-29, a force magnifier 1300 may be similar or identical to force magnifier 100 except that force magnifier 1300 includes a front tab 1310 and a rear tab 1320 to allow releasable connection to a bone plate, such as bone plate 202 or bone plate 1202, instead of engaging surface 102 of force magnifier 100. Front tab 1310 may extend or "toe into" a hole (e.g., hole 1205) or a cutout of such a hole (e.g., one of cutouts 1250) while rear tab 1320 may be resilient to allow it to be moved toward a remainder of the force magnifier and resiliently return such that the rear tab connects to, and "clicks into", the hole and/or cutout. FIGS. 26 and 27 depict force magnifier 1300 received in hole 1205 with front tab 1310 and rear tab 1320 received in cutouts 1250. FIG. 28 shows force magnifier 1300 above hole 1205 and FIG. 29 depicts force magnifier 1300 angled to allow front tab 1310 to be inserted into one of cutouts 1250. After such insertion force magnifier 1300 may be manipulated such that rear tab 1320 may engage a second of cutouts 1250 longitudinally opposite the first of cutouts 1250. In a further example depicted in FIGS. 30-31, a force magnifier 1400 may be similar or identical to force magnifier 1300 except that force magnifier 1400 may be connected to a handle 1410. As depicted in FIG. 31, handle 1410 may be manipulated such that force magnifier 1300 connects to bone plate 1202. For example, force magnifier 1400 may be manipulated by a user using handle 1410 such that a front tab 1409 similar front tab 1310 may be inserted into one of cutouts 1250 and a rear tab (not shown) similar to rear tab 1320 may engage a second of cutouts 1250 longitudinally opposite the first of cutouts 1250.

Figure 32:
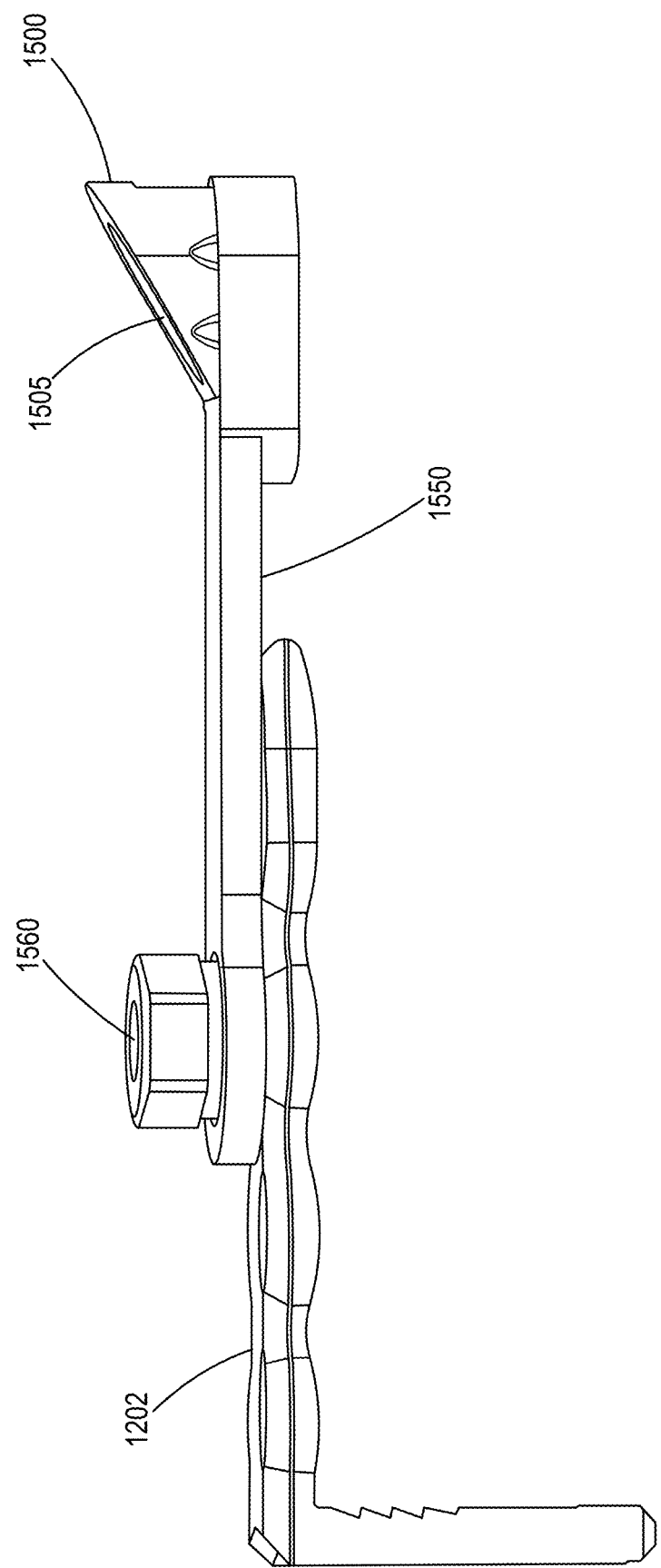
FIG. 32 is a side view of a compression force magnifier having an arm connectable to a bone plate with the compression force magnifier laterally separated from the bone plate in accordance with an aspect of the present invention.

In an example depicted in FIG. 32, a force magnifier 1500 may be similar or identical to force magnifier 1300 except that force magnifier 1500 may include an arm 1550 having a hole 1560, which may be threaded, for connection of the arm to a bone plate (e.g., bone plate 202 or bone plate 1202) via a screw (e.g., 112) or other attachment mechanism. Force magnifier 1500 may be attached to a first bone portion (not shown) separated from a second bone portion (not shown) connected to a bone plate (e.g., bone plate 202 or bone plate 1202) connected to force magnifier 1500. When force magnifier 1500 is connected to the first bone portion and arm 1550 thereof is connected to the second bone portion, the first and second bone portions may be moved toward each other as described above relative to compression force magnifier 100 and bone plate 202 except that force magnifier 1500 is connected to the bone plate by the arm and not directly via a hole therein. Specifically, a hole 1505 in force magnifier 1500 similar to hole 110 in force magnifier 100 is separated from the bone plate and thus the first bone portion may be separated from the plate and moved toward the plate by the action of a screw or other attaching member received in hole 1505 of force magnifier 1500 and connected to the second bone portion. The separation of a force magnifier (e.g., force magnifier 1500) from a bone plate (e.g., bone plate 1202) while being connected by an arm (e.g., arm 1550) of the force magnifier (or releasable arm attached thereto) allows the use of the force magnifier in situations of trauma such as or for long bones where the bone would extend beyond a longitudinal dimension of a bone plate. Force magnifier 1500 may also be connected to a handle similar to handle 1410 described above relative to force magnifier 1400.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description; it is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A compression force magnifier, said compression force magnifier comprising:
   a body with a vertical axis therethrough;
   a proximal surface of said body sloped at a predetermined angle relative to said vertical axis;
   a flat distal surface of said body, said distal surface disposed opposite said proximal surface;
   a bore disposed through said body from said proximal surface through said distal surface; and
   said body connected to an arm having a connection opening configured to allow connection of said body to a bone plate having a plate apertured configured for connection to a first bone portion, said connection opening having a connection axis spaced from said bore;
   said proximal surface sloped at said predetermined angle such that said proximal surface is inclined upwardly in a direction away from said connection opening to allow a lateral force to be placed in a direction away from the bone plate and toward said body configured to cause a movement of said first bone portion and a second bone portion toward each other when a screw is received in said bore to apply a vertical force to said body configured and to connect said body to said second bone portion.

2. The compression force magnifier of claim 1 wherein said connection opening is spaced from said bore in a longitudinal direction relative to a longitudinal dimension of said arm.

3. The compression force magnifier of claim 1 wherein said connection axis is non-coaxial relative to said vertical axis.

4. The compression force magnifier of claim 1 further comprising a handle connected to the body to allow a user to manipulate the body.

5. A bone compression system, said system comprising:
   a bone plate, said plate having a proximal plate surface and a bone contacting plate surface disposed opposite said proximal plate surface, said bone plate further comprising a plate aperture disposed through said plate between said proximal plate surface and said bone contacting plate surface configured to allow connection of said bone plate to a first bone portion; and
   a compression force magnifier comprising:
      a body having a proximal body surface and a distal surface opposite said proximal surface;
      a bore disposed through said body from said proximal surface through said distal surface configured to allow connection of said body to a second bore portion, said bore having a bore axis;
      said proximal body surface of said body sloped at a predetermined angle relative to said bore axis;
      said body connected to an arm having a connection opening configured to allow connection of said body to said bone plate, said connection opening having a connection axis spaced from said bore axis;
      said proximal body surface sloped at said predetermined angle such that said proximal body surface is inclined upwardly in a direction away from said connection opening and said bone plate to allow a lateral force to be placed in a direction away from said bone plate and toward said body configured to cause a movement of said first bone portion and said second bone portion toward each other when a screw is received in said bore configured to connect said body to said second bone portion and to apply a vertical force to said body and a second screw is configured to be connected through said plate aperture to said first bone portion.

6. The system of claim 5, wherein said compression force magnifier is releasably attached to said bone plate.

7. The system of claim 5 further comprising a fastener connecting said bone plate to said arm through said connection opening and said plate aperture.

8. The system of claim 5 further comprising a handle connected to the body to allow a user to manipulate the body.

* * * * *